United States Patent [19]

Companion

[11] Patent Number: 5,053,341

[45] Date of Patent: Oct. 1, 1991

[54] TISSUE SIMULATING GEL FOR MEDICAL RESEARCH

[75] Inventor: John A. Companion, Hampton, Va.

[73] Assignee: The United States of America as represented by the Administrator of the National Aeronautics and Space Administration, Washington, D.C.

[21] Appl. No.: 418,372

[22] Filed: Oct. 6, 1989

[51] Int. Cl.$^5$ .................. B01J 13/00; G01N 31/00
[52] U.S. Cl. .................. 436/8; 252/315.1; 252/518; 252/962; 436/64; 436/147; 436/176
[58] Field of Search .............. 252/315.1, 962, 518; 436/15, 8, 64, 147, 176; 128/742; 374/57

[56] References Cited

U.S. PATENT DOCUMENTS

| | | | |
|---|---|---|---|
| 2,124,767 | 7/1938 | Dawn | 2/206 |
| 2,555,037 | 5/1951 | Jensen | 252/521 X |
| 3,658,726 | 4/1972 | Mühl | 252/518 |
| 3,988,479 | 10/1976 | Stephan et al. | 426/1 |
| 4,277,367 | 7/1981 | Madsen et al. | 436/8 |
| 4,496,357 | 1/1985 | Osburn | 252/315.1 X |
| 4,913,897 | 4/1990 | Chvapil et al. | 252/315.1 X |

Primary Examiner—Richard D. Lovering
Attorney, Agent, or Firm—Kevin B. Osborne; George F. Helfrich

[57] ABSTRACT

A tissue simulating gel and a method for preparing the tissue simulating gel are disclosed. The tissue simulating gel is prepared by a process using water, gelatin, ethylene glycol, and a cross-linking agent. In order to closely approximate the characteristics of the type of tissue being simulated, other material has been added to change the electrical, sound conducting, and wave scattering properties of the tissue simulating gel. The result of the entire process is a formulation that will not melt at the elevated temperatures involved in hyperthermia medical research. Furthermore, the tissue simulating gel will not support mold or bacterial growth, is of a sufficient mechanical strength to maintain a desired shape without a supporting shell, and is non-hardening and non-drying. Substances have been injected into the tissue simulating gel prior to the setting-up thereof just as they could be injected into actual tissue, and the tissue simulating gel is translucent so as to permit visual inspection of its interior. A polyurethane spray often used for coating circuit boards can be applied to the surface of the tissue simulating gel to give a texture similar to human skin, making the tissue simulating gel easier to handle and contributing to its longevity.

20 Claims, No Drawings

TISSUE SIMULATING GEL FOR MEDICAL RESEARCH

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 USC 2457).

BACKGROUND OF THE INVENTION

1. Field of the Invention

This invention relates to a composition and a method for producing a tissue simulating gel. More specifically, the invention is a simulated soft human or animal tissue particularly applicable in the field of medical research because it will not melt at elevated temperatures, it is non-hardening and non-drying for extended periods of time, and it will not support bacterial growth.

2. Description of the Prior Art

Many formulae currently exist for producing tissue simulating gels. A number of these formulae are based on agars, simple hydrated collagen gels, or polyacrylamides. These formulae often suffer from deficiencies which make them ill-suited for extended medical research: hydrated gels tend to dry out; some gels melt at the elevated temperatures involved in research; others become hosts for micro-organisms; some are too expensive or too difficult to make to be of practical value.

Using a plasticizing agent such as ethylene glycol and a coagulating or precipitating agent such as formaldehyde in preparing a substance which gives the appearance of flesh was described in U.S. Pat. No. 2,124,767 (Dawn). The invention disclosed in Dawn pertains primarily to the preparation of a masking substance used to disguise or change the appearance of an individual, particularly for acting purposes. The simulated flesh developed in Dawn is substantially dehydrated: it is prepared using ethylene glycol and water in proportions of approximately 2 to 1 respectively, following which the water is condensed out of the formulation using a pressure cooker. Dawn uses approximately 30 percent by weight of gelatin and less than 1 percent by weight of formaldehyde. One of the advantages of the Dawn formulation is its ability to withstand the heat of stage lights, though the formulation will melt and can be molded to an individual's skin using hot water.

Aside from appearance, the substance disclosed in Dawn has no other characteristics of human flesh, and it is therefore inappropriate for medical research. Unlike actual tissue, which is substantially water, the Dawn formulation after processing is substantially dehydrated. Furthermore, the Dawn formulation does not have the electrically conducting characteristic of actual tissue, nor does it have the sound conducting and wave scattering properties of actual tissue. Its ability to be melted with hot water while being molded to an individual's skin indicates it will not withstand the temperatures frequently encountered in hyperthermia research. Furthermore, because the Dawn formulation is produced using a pressure cooker, it is impractical to inject material into the substance to alter its properties before the substance sets. Once the substance has set, injection of any material will cause tearing.

SUMMARY OF THE INVENTION

The present invention is a new composition of matter and a process for producing it.

An object of the present invention is to produce an animal or human tissue simulating gel that will be useful in medical research.

A further object of the present invention is a tissue simulating gel that does not melt at elevated temperatures experienced in hyperthermia research, does not dry-out nor harden for extended periods of time, and does not support the growth of micro-organisms.

A further object of the present invention is to provide a process for producing a tissue simulating gel such that before the gel sets, material can be injected or imbedded into it at such a point that the material will remain suspended in the tissue simulating gel once it sets, and the injection will not cause tearing of the tissue simulating gel.

To meet the foregoing objects, a tissue simulating gel and method for producing it have been developed. The new gel includes ethylene glycol, water, a cross-linking agent such as formaldehyde, and gelatin. Filler material and electrically conducting chemicals can be added to the gel to more closely approximate the characteristics of actual tissue. Glycerol can also be added to the mixture to give the tissue simulating gel a more rubbery characteristic which allows the gel to withstand handling somewhat better.

Initially, if desired, a soluble electrically conducting material is added to and dissolved in the water. It has been found that adding potassium chloride or sodium chloride is especially beneficial for this purpose. Next, about 80 grams to about 100 grams of gelatin is added to the water solution. It has been found that 100 grams of 175 to 300 Bloom gelatin per 1 liter of final solution of water and ethylene glycol works well, with 175 Bloom gelatin yielding a somewhat softer tissue simulating gel. The ethylene glycol is then added to the water solution in a proportion to water which is between 50 to 50 and 65 to 35. Using substantially equal amounts of ethylene glycol and water has been found to be especially beneficial. At this point, the mixture is heated and stirred continuously to melt the gelatin. As soon as the gelatin melts, the mixture is removed from the heat. The material then can be deaerated and stored. If the material is stored, it will solidify, and will need to be remelted before adding the cross-linking agent. The cross-linking agent is added in an amount equivalent to between about 20 grams and about 40 grams of formaldehyde per 1 liter of ethylene glycol and water solution. It has been found to be especially preferred to use about 75 milliliters of a 37% aqueous solution formaldehyde per 1 liter of solution of water and ethylene glycol. The pot life of the mixture after the cross-linking agent has been added is highly dependent on the temperature of the solution at the time the cross-linking agent is added. If the solution is hot when the cross-linking agent is added, the gel will set-up within a few seconds. Therefore, it is more desirable to add the cross-linking agent after the mixture has cooled. If the cross-linking agent is added when the solution is cooled to a temperature just above the temperature at which the solution would normally set (approximately 32° C.), the pot life will be about 55-60 minutes.

Once the viscosity of the solution has reached a point at which it will suspend particles, filler material may be added to mimic the sound conducting and wave scattering properties of a particular type of tissue being simulated. Typically, the mixture will reach the desired viscosity during the last ten of the sixty minutes during which the gel sets.

The tissue simulating gel, during the viscous phase, has a sticky characteristic viscous enough to allow the insertion of hypodermic needles and catheters without tearing. Moreover, the resulting tissue simulating gel is translucent, allowing visual inspection of the interior. A polyurethane coating can be sprayed on or applied to the tissue simulating gel to give it the texture of skin and increase the longevity thereof by further protecting it from dehydration. The tissue simulating gel is especially suitable for hyperthermia medical research: it is non-hardening and non-drying for extended periods of time, and it will not melt at the elevated temperatures involved in such research. Furthermore, the tissue simulating gel will not support the growth of micro-organisms.

DESCRIPTION OF THE PREFERRED EMBODIMENT

The present invention is a new composition of a tissue simulating gel and a method for producing it.

Hyperthermia cancer research often requires a simulated tissue to conduct electricity in order for microwaves, which are used to produce the hyperthermia, to react with the simulated tissue in the same manner as they would react with actual tissue. Therefore, if the particular research for which the tissue simulating gel will be used requires the tissue simulating gel to conduct electricity, the first step of the process is to dissolve enough sodium chloride into about 0.5 liters of distilled water to give the tissue simulating gel the dielectric constant of a particular body tissue being simulated. One-hundred grams of gelatin is then added to the solution. The gelatin should be added to the water when the water is cold (room temperature or below) to prevent lumping which results from adding the gelatin to hot water. A 175 Bloom gelatin is preferred over higher Bloom gelatins because the 175 Bloom gelatin yields a slightly softer characteristic in the final tissue simulating gel than higher Bloom gelatins.

Next, about 0.5 liters of ethylene glycol is added to and stirred into the mixture. Also, about 100 milliliters of glycerol per liter of solution of water and ethylene glycol can be added to impart a rubbery characteristic on the tissue simulating gel.

The mixture is heated slowly to about 38° to 45° C. while it is stirred constantly. The temperature of the mixture is maintained and the mixture is stirred until all the gelatin is dissolved.

As soon as the gelatin is completely dissolved, the solution should be removed from the heat in order to prevent water loss. The solution is then deaerated. De-aerating can be accomplished most easily by setting the mixture aside until all the air bubbles come to the surface and can be skimmed off. A more effective way to deaerate, however, is to use a vacuum pump, placing the solution under a partial vacuum. At this point, the material can be stored. Storing can often times be accomplished most easily in a covered plastic container. If stored, however, the material will solidify, but it can easily be remelted when needed by applying heat.

The next step in the process is to catalyze the material in its liquid state. Catalyzation is best accomplished when the solution is cooled to below 38° C. but above a temperature at which it begins to solidify (typically at 32° C. or below). This catalyzation is most easily accomplished by adding to the tissue simulating solution 100 milliliters of 37 percent formaldehyde solution per liter quantity of aqueous solution of ethylene glycol. The formaldehyde must be mixed thoroughly into the tissue simulating gel solution, and then the tissue simulating solution is poured into a mold. Generally when using 175 Bloom gelatin, the working life of the tissue simulating gel before it sets-up is approximately 60 minutes, although the working life is somewhat shorter when using higher Bloom gelatins.

During approximately the last ten minutes of the working life of the tissue simulating gel after catalyzation, the tissue simulating gel enters a viscous state during which various filler and other material can be imbedded into the tissue simulating gel and remain suspended in the tissue simulating gel after it sets-up. Examples of such imbedded materials include simulated tumors, cell wall simulating additives, or thermometry devices. A hypodermic needle can be used at this point to inject materials; after injection, the hole through which the needle passed will close. Proprietary wax compounds intended for hyperthermia cancer research can also be imbedded during this stage.

After the cross-linking has taken place and the tissue simulating gel has completely set-up, it can be removed from the mold and used without any supporting shell.

Sometimes it may be desired to apply a polyurethane coating to the surface of the gel to give the gel a texture similar to skin.

What is claimed is:

1. A process for producing a tissue simulating gel for use in hyperthermia research, the process comprising the steps of:

adding a gelatin to water to provide a desired rigidity;

mixing ethylene glycol to the water and gelatin to produce a mixture;

heating and constantly stirring this mixture at a temperature below approximately 45° C. to completely dissolve the gelatin such that water loss is prevented; and catalyzing the mixture by mixing an appropriate amount of formaldehyde therein as a cross-linking agent.

2. The process according to claim 1, wherein the ratio of ethylene glycol to water is between approximately 65:35 to 50:50 and an amount of gelatin added is such that between approximately 80 to 100 grams of gelatin are added per one liter of ethylene glycol and water.

3. The process according to claim 2, wherein between approximately 75 and 100 ml of 37 percent formaldehyde solution per one liter of ethylene glycol and distilled water are mixed into the mixture.

4. The process according to claim 2, wherein between approximately 20 and 40 grams of formaldehyde per one liter of ethylene glycol and water solution are mixed into the mixture.

5. The process according to claim 2, wherein the gelatin is between approximately 175 and 300 Bloom.

6. The process according to claim 2, further comprising adding approximately 100 ml of glycerol per one liter of the mixture of water, ethylene glycol and gelatin to said mixture.

7. The process according to claim 1, further comprising adding glycerol to the mixture of water, ethylene glycol and gelatin.

8. The process according to claim 1, further comprising the additional first step of dissolving a soluble electrically conducting chemical compound in the water.

9. The process according to claim 1, further comprising applying a polyurethane coating to the surface of the tissue simulating gel.

10. The process according to claim 1, wherein said catalyzing step occurs after the mixture has cooled to a temperature just above a temperature at which the mixture would normally set.

11. A tissue simulating gel for use in hyperthermia research produced by a process comprising the steps of:
adding a gelatin to water to provide a desired rigidity;
mixing ethylene glycol to the water and gelatin to produce a mixture;
heating and constantly stirring this mixture at a temperature below approximately 45° C. to completely dissolve the gelatin such that water loss is prevented; and
catalyzing the mixture by mixing an appropriate amount of formaldehyde therein as a cross-linking agent.

12. The gel according to claim 11, wherein the ratio of ethylene glycol to water is between approximately 65:35 to 50:50 and an amount of gelatin added is such that between approximately 80 to 100 grams of gelatin are added per one liter of ethylene glycol and water.

13. The gel according to claim 12, wherein the gelatin is between approximately 175 and 300 Bloom.

14. The gel according to claim 12, further comprising adding approximately 100 ml of glycerol per one liter of the mixture of water, ethylene glycol and gelatin to said mixture.

15. The gel according to claim 11, wherein between approximately 75 and 100 ml of 37 percent formaldehyde solution per one liter of ethylene glycol and water are mixed into the mixture.

16. The gel according to claim 11, wherein between approximately 20 and 40 grams of formaldehyde per one liter of ethylene glycol and water solution are mixed into the mixture.

17. The gel according to claim 11, further comprising adding glycerol to the mixture of water, ethylene glycol and gelatin.

18. The gel according to claim 11, further comprising the additional first step of a soluble electrically conducting chemical compound in the distilled water.

19. The gel according to claim 11, further comprising a polyurethane coating applied to the surface of the tissue simulating gel.

20. The gel according to claim 11, wherein said catalyzing step occurs after the mixture has cooled to a temperature just above a temperature at which the mixture would normally set.

* * * * *